US00PP25850P3

(12) United States Plant Patent
Jury

(10) Patent No.: US PP25,850 P3
(45) Date of Patent: Sep. 1, 2015

(54) ***MICHELIA* PLANT NAMED 'MICJUR02'**

(50) Latin Name: ***Michelia yunnanensis*×hybrid**
Varietal Denomination: MicJur02

(71) Applicant: Mark Jury, Waitara (NZ)

(72) Inventor: Mark Jury, Waitara (NZ)

( * ) Notice: Subject to any disclaimer, the term of this patent is extended or adjusted under 35 U.S.C. 154(b) by 167 days.

(21) Appl. No.: 13/987,703

(22) Filed: Aug. 21, 2013

(65) Prior Publication Data

US 2015/0059031 P1 Feb. 26, 2015

(51) Int. Cl.
*A01H 5/00* (2006.01)

(52) U.S. Cl.
USPC ..... Plt./226

(58) Field of Classification Search
USPC ..... Plt./226, 216
See application file for complete search history.

(56) References Cited

PUBLICATIONS

PLUTO Plant Variety Dtabase Mar. 30, 2015 p. 1.*

* cited by examiner

*Primary Examiner* — Annette Para
(74) *Attorney, Agent, or Firm* — Cassandra Bright

(57) ABSTRACT

A new and distinct *Michelia* cultivar named 'MICJUR02' is disclosed, characterized by having a robust, compact growth habit and abundant masses of fragrant, creamy white flowers. Plants are evergreen and tolerate pruning and shaping very well, making them useful as a hedge, topiary or specimen tree. The new variety is a *Michelia*, normally produced as a small ornamental tree.

2 Drawing Sheets

Latin name of the genus and species: *Michelia yunnanensis*×hybrid.

Variety denomination: 'MicJur02'.

BACKGROUND OF THE INVENTION

The new cultivar is a product of a planned breeding program. The new variety resulted from a crossing performed in 1995 in North Taranaki, Nth Is, New Zealand. The seed parent is the unpatented variety, *Michelia yunnanensis* 'Velvet and Cream'. The pollen parent is the unpatented variety *Michelia* hybrid 'Mixed Up Miss'. The new variety was first selected in 1999, by the inventor, Mark Jury at a commercial nursery in North Taranaki, New Zealand.

Asexual reproduction of the new cultivar 'MicJur02' by vegetative cuttings was first in performed in 2004 at a commercial nursery in New Zealand and has shown that the unique features of this cultivar are stable and reproduced true to type on successive generations.

SUMMARY OF THE INVENTION

The cultivar 'MicJur02' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MicJur02'. These characteristics in combination distinguish 'MicJur02' as a new and distinct *Michelia* cultivar:

1. Small to medium sized evergreen tree.
2. Abundant masses of flowers.
3. Compact growth habit.
4. Creamy white flowers.

5. Strong fragrance to flowers.
6. Usefulness as a street tree, hedge, topiary or specimen tree.
7. Suitability for pruning and shaping.

PARENT COMPARISON

Plants of the new cultivar 'MicJur02' are similar to plants of the seed parent, *Michelia yunnanensis* 'Velvet and Cream' in most horticultural characteristics, however, plants of the new cultivar 'MicJur02' have larger flowers and larger foliage. Additionally, plants of the new variety produce fragrant flowers, whereas the seed parent produces unscented flowers.

Plants of the new cultivar 'MicJur02' are similar to plants of the pollen parent, *Michelia* hybrid. 'Mixed up Miss' in most horticultural characteristics, however, plants of the new cultivar 'MicJur02' have flowers which are more heavily scented. Additionally, plants of the new variety are shorter and more compact, with smaller, lighter colored foliage than the pollen parent.

BRIEF DESCRIPTION OF THE PHOTOGRAPH

Figure 1:
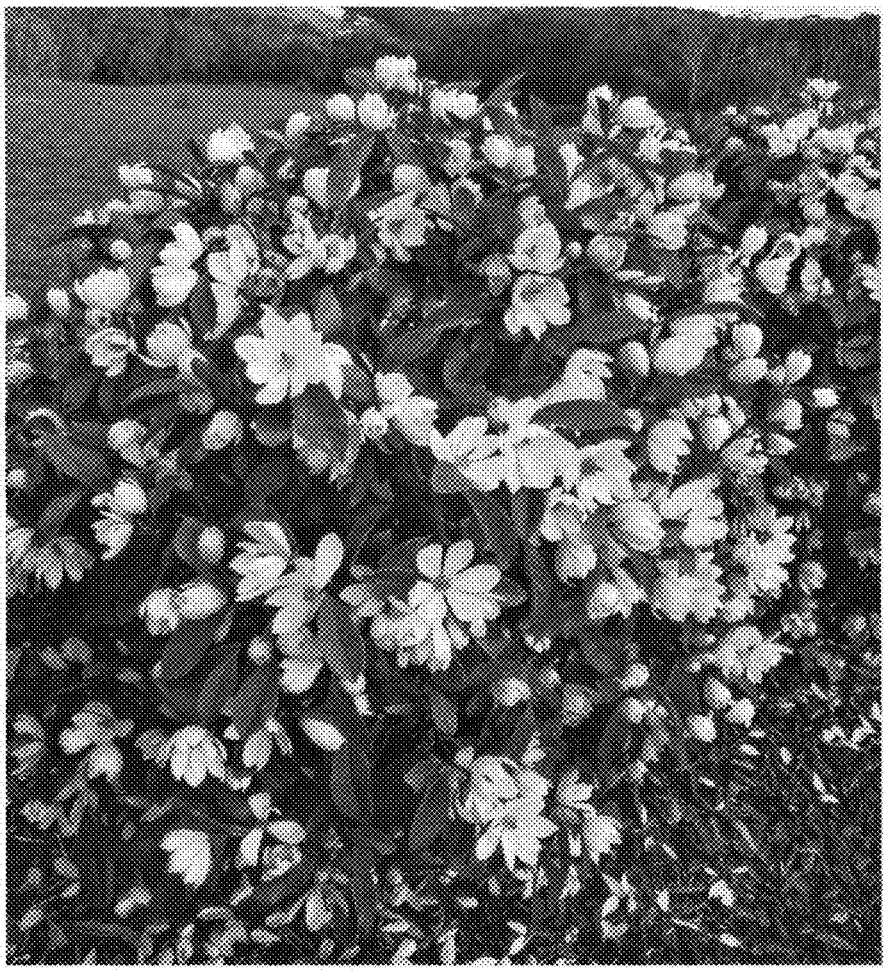

The accompanying photograph in FIG. 1 illustrates in full color a typical plant of 'MicJur02' outdoors. Age of the plant photographed is approximately 5 years from a rooted cutting.

Figure 2:
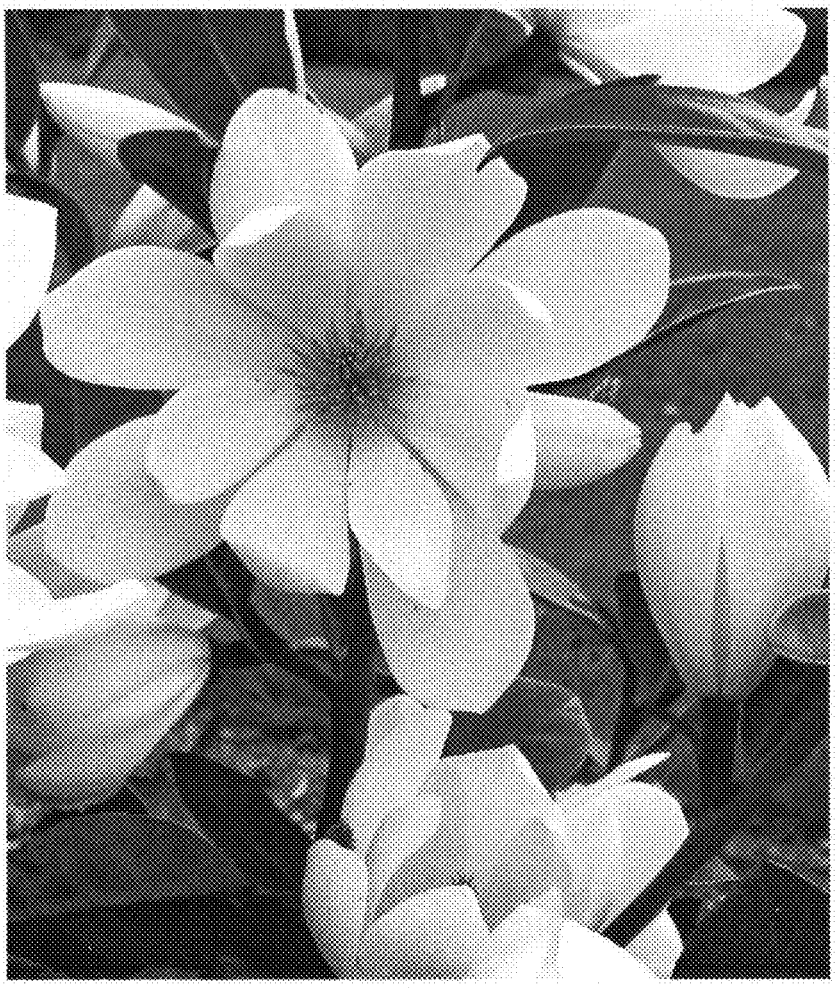

FIG. 2 illustrates in full color typical flowers of 'MicJur02'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MicJur02' plants grown outdoors in New Zealand. Growing conditions are similar to USDA Zone 7. Age of the plants when described is approximately 4 years old. Measurements and numerical values represent averages of typical plant types.

Botanical classification: *Michelia yunnanensis*×hybrid 'MicJur02'.

PROPAGATION

Time to initiate roots: About 60 days at approximately 21° C.
Time to produce a rooted cutting: About 120 days at 21° C.
Root description: Typical *Michelia* root, thick, coarse, colored near RHS White 155A.

PLANT

Growth habit: Upright, spreading small evergreen tree.
In a container or in the ground: Ground.
Height: Approximately 4 meters after 12 years.
Plant spread: Approximately 3 meters after 12 years.
Stem diameter: Approximately 17 cm after 12 years.
Branching characteristics: Depends upon cultural techniques. Without pruning, a Normally a single trunk tree with lateral branches forming at acute angles to the trunk. With pruning, plants can be grown as large shrubs.
Individual branch characteristics (of 1 year old tree):
- *Length.*—Up to 20 cm.
- *Diameter.*—Up to 0.5 cm.
- *Texture.*—Smooth.
- *Color.*—Near RHS 197B.

Trunk:
- *Diameter.*—Approximately 17 cm, after 12 years. Measured approximately 10 cm above the ground.
- *Texture.*—Smooth.
- *Color.*—Near RHS 197B.

FOLIAGE

Leaf:
- *Arrangement.*—Mixed alternate, and occasionally opposite.
- *Average length.*—Approximately 12.5 to 14.5 cm.
- *Average width.*—Approximately 5.5 to 6.0 cm.
- *Shape of blade.*—Elliptic.
- *Apex.*—Acute to acuminate.
- *Base.*—Rounded.
- *Margin.*—Entire.
- *Texture of top surface.*—Smooth, with glossy appearance.
- *Texture of lower surface.*—Smooth.
- *Leaf internode length.*—Approximately 3 cm.
- *Color.*—Mature foliage upper side: Near RHS Yellow-Green 147A. Mature foliage under side: Near RHS Yellow-Green 146B, with a pale brown cast near Grey-Green 197A.

Foliage:
- *Venation.*—Type: Pinnate. Venation color upper side: Near RHS Yellow-Green 144C. Venation color under side: Near RHS Yellow-Green 144B. Petiole: Not present, sessile.

FLOWER

Natural flowering season: Flowering begins mid Spring. Lasts approximately 8 weeks.
Begins flowering after how many years/months: 1.5 to 2 years after planting an unrooted cutting.
Inflorescence type and habit: Solitary occurring, rotate, flattened concave flowers. Profuse flowering.
Quantity of flowers: Profuse, thousands per tree.
Inflorescence size:
- *Diameter.*—Approximately 10 to 12.5 cm.
- *Length.*—Approximately 6 cm.

Peduncle:
- *Length.*—10 to 15 cm.
- *Diameter.*—0.5 cm.
- *Color.*—Near RHS Greyed-Orange 166A.
- *Texture.*—Soft velvety pubescence.

Pedicel: Not present.
Petals:
- *Petal arrangement.*—9 to 13 whorled, overlapping.
- *Shape.*—Elliptic.
- *Size.*—Length: 2.5 to 3.0 cm. Width: 6.0 to 6.5 cm.
- *Margin.*—Entire.
- *Apex.*—Acute.
- *Base.*—Rounded.
- *Petal quantity.*—Approximately 9 to 13.
- *Texture.*—Smooth.

Color:
- *Petals.*—When opening: Upper surface: Near RHS White N155A, base Yellow-Green 154C. Lower surface: Near RHS Yellow-Green 154C. Fully opened: Upper surface: Near RHS White N155A, base Yellow-Green 154C. Lower surface: Near RHS Yellow-Green 154C. Color Changes when aging: Upper surface: Near RHS White N155A, base Yellow-Green 154C. Lower surface: Near RHS Greyed-Yellow 160A.

Bud:
- *Shape.*—Ovate to linear.
- *Length.*—Approximately 2 cm.
- *Diameter.*—Approximately 1 cm.
- *Color.*—Near RHS Greyed-Orange 166B.

Sepals/tepals: Not Present.
Fragrance: Noticeable strong fragrance.

REPRODUCTIVE ORGANS

Stamens:
- *Number.*—Approximately 25.
- *Filament length.*—Approximately 1.5 cm.
- *Filament color.*—Near RHS Greyed-Yellow161B.

Anthers:
- *Length.*—Approximately 0.2 cm.
- *Shape.*—Linear.
- *Color.*—Near RHS Orange-White 159A.

Pistil:
- *Number.*—1.
- *Length.*—Approximately 2 cm.
- *Style.*—Length: Approximately 1.8 cm. Color: Near RHS Yellow-Green 144A when immature. Matures to Greyed-Orange 166B.
- *Pollen.*—Quantity: Moderate. Color: Near RHS Greyed-Orange 163B.

OTHER CHARACTERISTICS

Seeds and fruits: The new cultivar does not set seed. Small, dry fruit produced, not reaching maturity and dropping after approximately 10 days.

*Fruit color.*—Begins near RHS Green Yellow-Green 144C, changes to Brown 200B before dropping.

*Size.*—Approximately 0.7 cm long, 0.2 cm wide.

Disease/pest resistance: Neither resistance nor susceptibility to pathogens and pests common to *Michelia* have been observed.

Temperature tolerance: The new variety is suitable for growing in USDA zones 7b through 11.

What is claimed is:

1. A new and distinct cultivar of *Michelia* plant named 'MicJur02' as herein illustrated and described.

* * * * *